Figure 1:
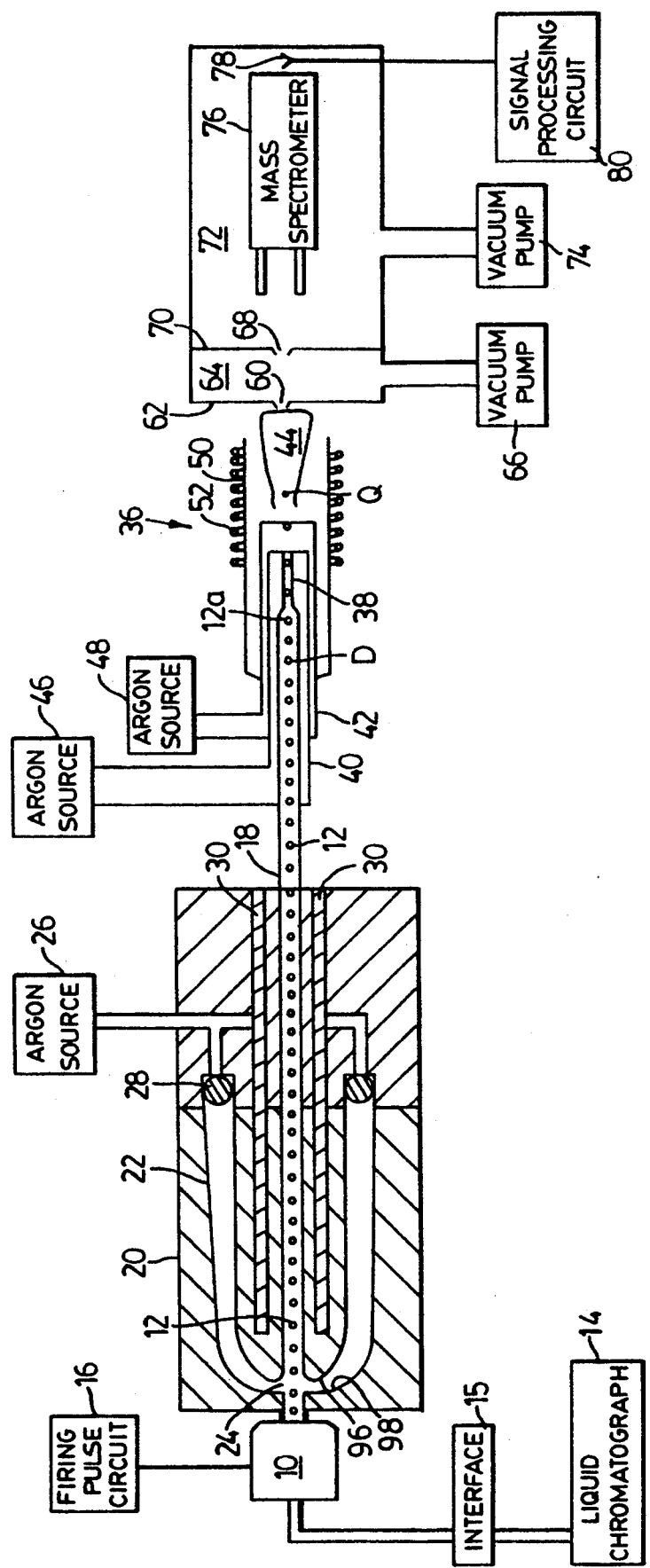

United States Patent [19]

French et al.

[11] Patent Number: 5,345,079
[45] Date of Patent: Sep. 6, 1994

[54] APPARATUS AND METHOD FOR LIQUID SAMPLE INTRODUCTION

[75] Inventors: John B. French, Oakville; Bernard Etkin, North York, both of Canada

[73] Assignee: MDS Health Group Limited, Etobicoke, Canada

[21] Appl. No.: 946,118

[22] Filed: Sep. 17, 1992

[30] Foreign Application Priority Data

Mar. 10, 1992 [CA] Canada .................................. 2062629

[51] Int. Cl.$^5$ ........................ B01D 59/44; H01J 49/00
[52] U.S. Cl. ..................................... 250/288; 250/282
[58] Field of Search ............ 250/281, 282, 288, 288 A

[56] References Cited

U.S. PATENT DOCUMENTS

| | | | |
|---|---|---|---|
| 4,070,286 | 1/1978 | Iler et al. | 210/31 C |
| 4,403,147 | 9/1983 | Melera et al. | 250/288 A |
| 4,470,699 | 9/1984 | Gay | 356/316 |
| 4,794,086 | 12/1988 | Kasper | 436/36 |
| 4,883,958 | 11/1989 | Vestal | 250/282 |
| 4,955,717 | 9/1990 | Henderson | 250/288 |
| 5,096,615 | 3/1992 | Prescott et al. | 250/288 |
| 5,170,052 | 12/1992 | Kato | 250/288 |

*Primary Examiner*—Bruce C. Anderson
*Attorney, Agent, or Firm*—Bereskin & Parr

[57] ABSTRACT

A liquid sample to be analyzed is fed to a micro pump. The pump directs the solution, as a stream of uniformly sized and spaced droplets, into a laminarly flowing stream of hot carrier gas. The carrier gas evaporates the solvents (e.g. water) in the droplets to form a stream of dried particles. The particles are vaporized by a plasma, laser or other heat source. The vapour can be ionized and the ions analyzed by a mass spectrometer, or the vapour can be analyzed by optical spectroscopy. The method reduces oxide and other interference effects, increases sample utilization, and reduces waste, signal noise, and memory effects, increasing instrument productivity. Multiple nozzles can be used to change samples or to shoot calibrating droplets, further increasing productivity. Signal detection can be synchronized with droplet firing, or the signal, which is intrinsically modulated at the drop frequency, can be band pass filtered and synchronously detected, to increase the signal to noise ratio. The dried particles can also be directed into a vacuum chamber and deposited in a desired pattern on a surface in the vacuum, thus delivering controlled microdosages of material onto the surface.

58 Claims, 10 Drawing Sheets

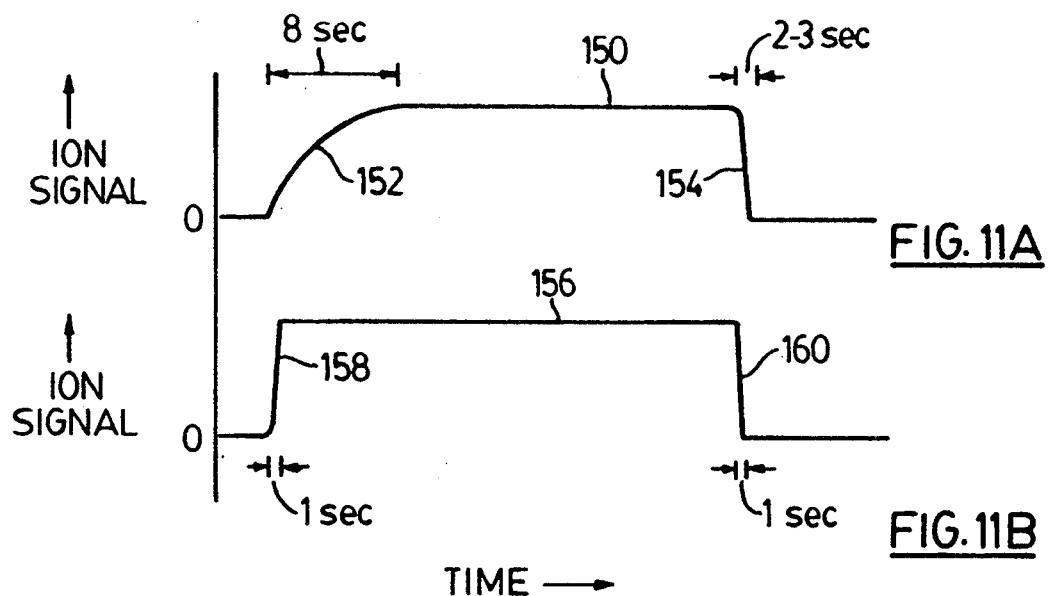
FIG. 11A
FIG. 11B
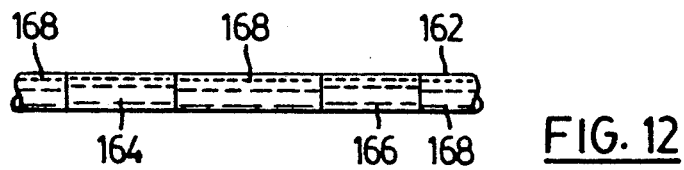
FIG. 12
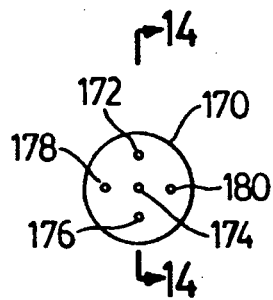
FIG. 13
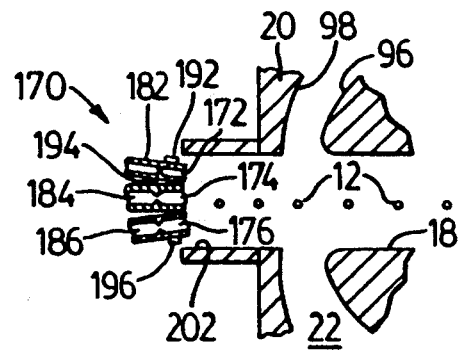
FIG. 14

APPARATUS AND METHOD FOR LIQUID SAMPLE INTRODUCTION

FIELD OF INVENTION

This invention relates to a method and apparatus for producing a controlled stream of dry micro particles from a liquid solution. In a preferred application, it relates to producing such a stream from a liquid sample, vaporizing the dried micro particles, and then analyzing them using a suitable analyzer. In another aspect it relates to delivering controlled micro-dosages of substances in the form of individual, or a stream of, dry micro particles onto a surface in a vacuum.

BACKGROUND OF THE INVENTION

Analyzers such as mass spectrometers or optical spectrometers are commonly used to perform chemical analyses. The most common form of sample used in such analyses is a liquid, often formed by dissolving the sample in dilute acid. The liquid sample is then sprayed into a hot plasma which largely vaporizes, atomizes and ionizes the elements in the sample. These elements then can be detected either by optical emission spectroscopy or by sampling the ions into a vacuum chamber for mass spectroscopy.

Commonly, pneumatic or sometimes ultrasonic nebulizers are used to introduce samples into plasmas. The nebulizers produce a fine spray having a distribution of drop sizes. A small portion of this distribution, consisting mostly of the smallest drops, is selected by a settling chamber and carried into the plasma by a sample gas stream (commonly argon), where it is vaporized by the plasma. This method, although commonly used, has many disadvantages. One disadvantage is that it produces a noisy signal, due to the statistics of both drop size distribution and drop arrival time and position in the plasma. Another disadvantage is that oxide interferences (unwanted oxide compounds which complicate spectral interpretation) result from the solvent (commonly water) which evaporates and provides oxygen in the plasma. This can be mitigated by interposing heating and drying but conventional methods of implementing these steps add complication and deleterious effects (e.g. memory effects and sample loss).

A further disadvantage of the current methods is that nebulizers waste most of the sample, typically 95%. This is undesirable where only a limited quantity of sample is available, and it creates an increasingly important problem in sample handling and safe disposal of the acid waste when large amounts of acids and samples are involved. Finally, nebulizers, spray settling chambers and dryers all contribute to increased washout time, the required time between different samples to avoid cross-contamination (the so-called memory effect). This washout time reduces the productivity of the instrument.

Other approaches have been described to deal with some of the above problems. Trains of uniform sized (i.e. mono-dispersed) liquid droplets have been injected into the plasma to facilitate the study of the underlying processes of evaporation and vaporization. The droplet sizes used (60 to 80 microns in diameter) were considered to be too large for analytical usage, so a variant in this theme added a strong shear flow to shatter these droplets into smaller droplets.

Another approach which has been described utilizes a micro nebulizer which disperses the totality of a much smaller liquid sample in nebulized form directly into the plasma. This eliminates sample wastage and reduces memory effects and so is more suitable for coupling to automated sample injectors or to liquid chromatograph columns. However unlike the present invention (as will be described), the sample is injected into the plasma while still in liquid form, and poly-dispersed, with attendant disadvantages as will be clear from the following description.

BRIEF SUMMARY OF THE INVENTION

It is therefore an object of the invention to provide an improved method and apparatus for producing a sample from a liquid solution.

In one of its aspects, the invention provides a method of sampling a liquid solution containing dissolved solids, comprising:

(a) producing a stream of flowing carrier gas, (b) producing a stream of spaced small droplets from said solution, (c) introducing said stream of droplets into said stream of carrier gas and transporting said droplets with said carrier gas, (d) heating said droplets in said carrier gas to evaporate water from said droplets into said carrier gas, (e) transporting said droplets in said carrier gas until said droplets have substantially dried to form a stream of spaced dried particles, said particles containing solids from said solution.

In another aspect, the invention provides a method of analyzing solids dissolved in a liquid sample solution, comprising:

(a) directing said solution into a small chamber, (b) causing a pressure pulse to be applied to solution in said chamber to shoot a droplet of said solution from said chamber, (c) entraining said droplet in a stream of flowing carrier gas, (d) heating said droplet in said stream of carrier gas to evaporate water from said droplet into said carrier gas, (e) transporting said droplet in said carrier gas until said droplet is substantially dried to form a dried particle containing said solids, (f) vaporizing said dried particle to produce vapor therefrom, (g) and analyzing said vapor.

In another aspect, the invention provides apparatus for analyzing solids dissolved in a liquid solution, comprising:

(a) a chamber for said solution, said chamber having an outlet nozzle, and means coupled to said chamber for applying a pressure pulse to solution in said chamber to shoot a droplet of said solution from said nozzle at a selected speed, (b) conduit means coupled to said nozzle for receiving said droplet, (c) means for introducing a stream of carrier gas into said conduit means for said carrier gas to flow in said conduit means at a selected velocity, and to carry said droplet along said conduit means, (d) means for heating said droplet in said carrier gas, (e) said conduit means being sufficiently long for substantially all of the water in a said droplet to evaporate into said carrier gas leaving a substantially dried particle of said solids, (f) vaporizing means coupled to said conduit means for vaporizing said dried particle, (g) and analyzer means coupled to said vaporizing means for analyzing the vapour from said dried particle.

Further objects and advantages of the invention will appear from the following description, taken together with the accompanying drawings.

BRIEF DESCRIPTION OF THE DRAWINGS

In the attached drawings:

FIG. 1 is a diagrammatic sectional view showing apparatus according to the invention for sampling a liquid solution, and for analyzing the sample stream so produced;

FIG. 2 is a diagrammatic cross-sectional view of a liquid reservoir for producing a droplet stream;

FIG. 3 is a sectional view along lines 3—3 of FIG. 2;

FIG. 4 is a plot of signal versus time showing variation of atomic emission and ion emission during transit of a single large drop through the viewing region;

FIG. 5 is a plot showing the response of the FIG. 1 apparatus versus concentration;

FIG. 6 is a plot showing signal and oxide intensities versus velocity for the FIG. 1 apparatus;

FIG. 7 is a plot showing oxide intensity versus velocity;

FIG. 8 is a plot showing signal and oxide intensities versus velocity;

FIG. 8A is a graph for various temperatures showing signal intensity versus drop frequency;

FIG. 9 is a plot showing signal intensity versus time;

FIG. 10 is a plot showing relative standard deviation versus counting time;

FIG. 11 A–B are plots showing "washout" times for a conventional nebulizer and for the apparatus of FIG. 1;

FIG. 12 is a diagrammatic view showing sample slugs separated by water slugs in a tube;

FIG. 13 is a diagrammatic view showing a modified embodiment of the invention for producing multiple streams;

FIG. 14 is a side view of the apparatus of FIG. 13;

FIG. 15 is a diagrammatic side view showing a further modified embodiment of the invention for producing multiple streams;

FIG. 16 is an end view of the apparatus of FIG. 15;

FIG. 17 is a diagrammatic side view showing a modification of the apparatus of FIG. 15;

FIG. 18 is a block diagram showing synchronous detection apparatus according to the invention;

FIG. 19 is a block diagram of a circuit used to increase the signal to noise ratio;

FIG. 20 is a diagrammatic view of a prior art graphite furnace used in graphite furnace atomic absorption spectroscopy;

FIG. 21 is a diagrammatic view showing graphite furnace atomic absorption spectroscopy apparatus according to the invention;

FIG. 22 is a sectional view of the graphite furnace of FIG. 21 showing the path of carrier gas and particles therein;

FIG. 23 is a diagrammatic view of apparatus according to the invention for depositing material on a surface; and FIG. 24 is a view similar to that of FIG. 1 but showing another embodiment of the invention.

DETAILED DESCRIPTION OF PREFERRED EMBODIMENTS

Reference is first made to FIG. 1, which shows a preferred embodiment of the invention. The FIG. 1 apparatus includes a micro pump 10 which produces a stream of small, uniformly sized and uniformly spaced, droplets 12 from a liquid solution, e.g. a solution obtained from a liquid chromatograph 14 through interface 15, or from another suitable liquid source. As will be described, the micro pump 10 is essentially the same as that found in a computer ink jet printer. The micro pump 10 is supplied with a suitable electrical signal from a signal source 16, to control the droplet repetition rate or frequency. The droplets 12 are typically ejected from the micro pump 10 at a velocity of between 2 and 4 meters per second.

The droplets 12 are directed or shot down a narrow (e.g. 5 mm diameter) tube 18 located over much of its length in a metal block 20. Block 20 also contains an annular passage 22 which is concentric and coaxial with tube 18. Passage 22 joins tube 18 at location 24 which is carefully shaped and smoothed to avoid turbulence, as will be described. A carrier gas such as argon is supplied from reservoir 26 into passage 22 and flows through settling screens 28 in passage 22 before reaching location 24, to remove local turbulence in the flow of carrier gas.

The carrier gas from source 26 travels through passage 22, sweeps around the corner at location 24 and flows down tube 18 together with the droplets 12. As will be explained in more detail shortly, the flow of argon gas from source 26 is laminar and travels in tube 18 at approximately the same speed as that of the droplets 12. The laminar flow of argon gas at about the same speed as the droplets has the effect that the droplets do not create a significant wake as they flow down the tube 18, and are therefore less likely to interfere with one another.

The block 20 is heated to a substantial temperature, e.g. 700° C. by heater rods 30 which are located in the metal annulus of block 20 between the passage 22 and the inner tube 18. This heats the argon gas in tube 18 to the same temperature, e.g. 700° C. The heated argon flowing down tube 18 evaporates water from the drops 12. (The drops can alternatively be directly heated by microwave or other radiation or by one or more lasers.)

As the drops 12 proceed down the tube 18, the water in them is eventually evaporated, at a dryness point D. Point D is essentially the same for all drops since they are all (initially) the same size and have the same history. What remains is a stream of dried micro particles 12*a*, each of which may have the form of a crystal sponge. The water vapour which was in the micro particles 12*a* is now contained in the argon stream moving through tube 18 with the micro particles 12. Such water vapour is diffused throughout the cross-section of the argon stream.

The micro particles 12*a* are next injected into a conventional plasma or torch device generally indicated at 36. As is conventional, tube 18 narrows at injector 38 to accelerate the flow of argon (and hence the particles 12*a*) into the torch. Two outer concentric tubes 40, 42 provide outer flows of argon as is conventional, to improve the characteristics of the plasma 44 to be formed and to cool the walls of the tube 50. Tubes 40, 42 receive their argon from sources 46, 48 which direct argon into tubes 40, 42 in known manner.

An outer quartz tube 50 contains the plasma 44, which is generated by an induction coil 52 encircling the quartz tube 50. Such torches are well known, and one version of such a torch is shown in U.S. Pat. No. 4,501,965 issued Feb. 26, 1985, assigned to the assignee of the present invention. Plasma 44 can also be generated using microwaves or another suitable energy source.

As is well known, the plasma 44 supplies heat to atomize anything in the sample stream (here the micro particles 12a and the water vapour), and also provides free electrons to ionize the atoms of the micro particles. A portion of the ions so produced is directed through a "skimmer" or orifice 60 in an orifice plate 62 which forms the wall of a first vacuum chamber 64. Vacuum chamber 64 is evacuated by a vacuum pump 66. From chamber 64, the ion stream passes through another orifice 68 in another plate 70 into a second stage vacuum chamber 72 evacuated by a pump 74. Chamber 72 contains a mass spectrometer 76 having an ion detector 78 which produces and transmits an ion detection signal to a conventional signal processing circuit 80 which through a suitable software program analyzes the ion signal and produces an output signal for a display such as a mass spectrum.

Figure 2:
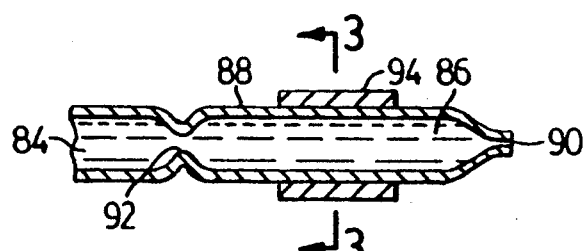
Figure 3:
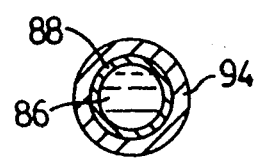
Figure 4:
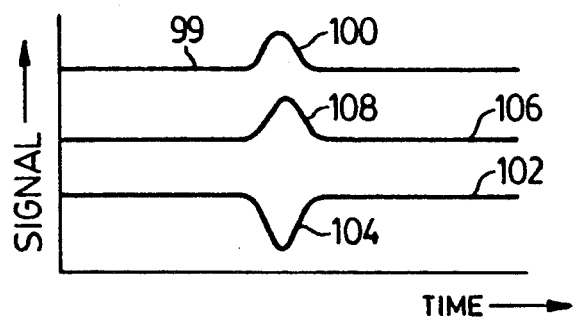
Figure 5:
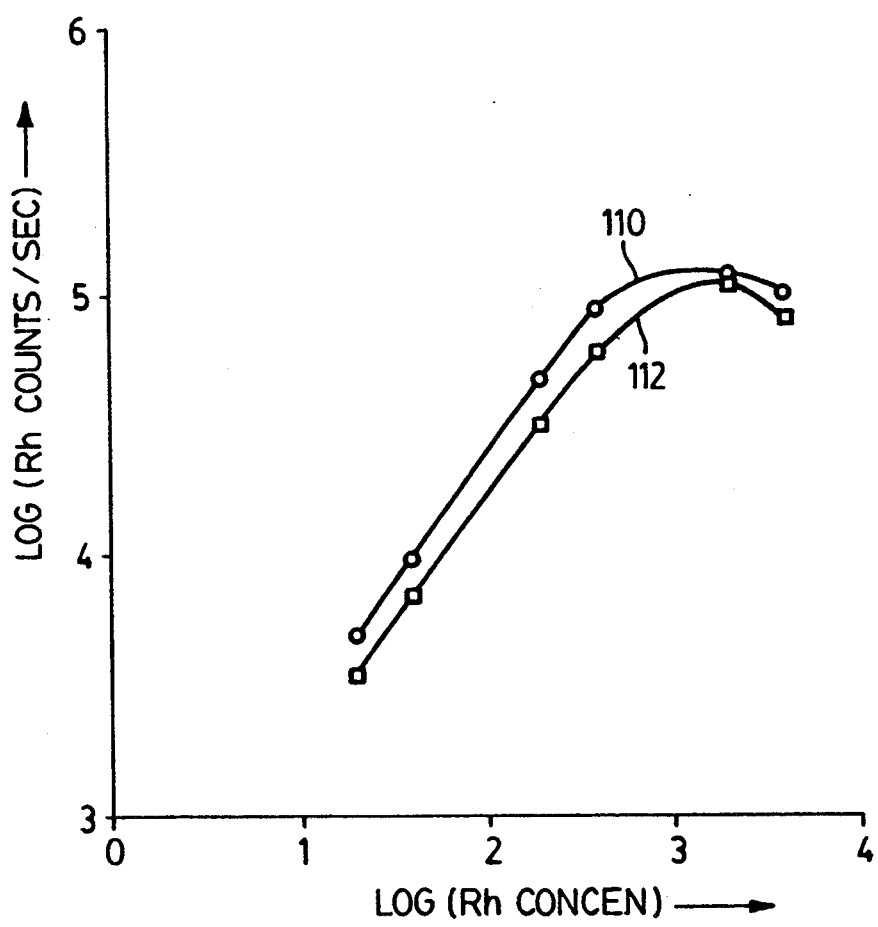

Reference is next made to FIGS. 2 and 3, which show the micro pump 10 in more detail. As indicated, the micro pump 10 is typically the same as that found in a conventional ink jet printer. A suitable pump of this kind is produced by Geselschaft Für Mikrodosiesysteme mbH of Germany. The micro pump 10 is thus conventional and will be described only briefly. As shown in FIGS. 2 and 3, it includes a passage 84 leading to a chamber 86 defined by a round glass tube 88. The chamber 86 terminates in a small tapered opening or nozzle 90 and is separated from the passage 84 by a constriction 92. An annular piezo-electric ceramic 94 encircles the tube 88 about the chamber 86 and, when a voltage is applied thereto, squeezes the chamber 86 slightly. This produces a pressure pulse in chamber 86, and because of the resistance to back flow caused by constriction 92, the pressure pulse shoots a liquid droplet 12 out nozzle 90. Typically, the micro pump 10 can operate at 0.1 to 3 KHz, although the frequency can be made much higher (e.g. 8 to 10 KHz), and can also be made much lower (e.g. droplets on demand, e.g. single droplets). Typically the droplets produced are of 60 to 80 microns in diameter and travel at between about 2 and 4 meters per second.

Other conventional controllable droplet generators can also be used, e.g. bubble jet drop generators in which an electrical pulse is applied to a heated wire behind the nozzle, creating a gas bubble and consequent pressure pulse which drives a liquid droplet out the nozzle. In both cases the electrical pulses are normally uniformly spaced apart and are of uniform duration and amplitude.

When a uniform train of droplets is injected into a co-flowing stream of gas, instability of the train may occur, manifested by the growth of irregularities in the drop spacing, and by lateral excursions of the drops. Such irregularities and excursions result from two basic causes, namely turbulence in the flow, and interference of the wakes of the droplets with adjacent droplets.

Since it is preferred to deliver a uniform regular stream of particle to the analysis means, any such irregularities and excursions should be minimized. Therefore the conveying gas stream should be laminar and steady, so that the stream velocity at any given point does not change with time. In other words, turbulence is avoided or minimized. The avoidance of wake interactions involves the interplay of two effects: drop spacing, and the drop/gas relative velocity vector. If the drops are far enough apart, their wakes will not affect adjacent drops. If the drop velocity vector and gas velocity vector are identical, then there are no wakes, and the drops can be very close together. The mismatch in velocity usually exists only during a transient phase immediately following injection of the droplets into the gas stream. The droplets subsequently turn (if the drop and stream velocity vectors are not initially aligned), and slow down or speed up (as the case may be), until their velocity vector matches that of the gas. The distance the drops travel during this transient phase depends on the drop size and the initial mismatch of velocity. Therefore, a combination of droplet size, droplet frequency, droplet injection velocity vector, and gas velocity vector should be chosen to yield the desired regularity and steadiness of the drop train.

In the embodiment depicted in FIG. 1, the droplets are injected into the tube 18 with an initial velocity vector that is parallel to the axis of the tube. It is noted that it is also possible to inject the droplets in other initial directions, including 90° to the axis of the tube. The injection at 90° to the tube axis requires a wider chamber and hence uses more argon or other carrier gas, but it can reduce oxide effects slightly since the water vapour evaporated from the droplets is then dispersed across a wider chamber (the oxide effects will be discussed in more detail presently).

Subsequent to the droplet injection, the flow of hot argon gas in which the droplets are entrained rapidly dries the droplets. As the droplets dry, their diameters decrease, again reducing wake effects. In addition, because the droplets rapidly lose mass as the water in them evaporates, they are less subject to gravity deflection as they flow through tube 18, so the unit can be operated horizontally if convenient. Also, once the droplets have been dried, the resulting particles are so small and light that they can more easily be piped around bends without loss (larger droplets are more likely to hit the tube walls, causing material loss and increased memory effects).

In practice, the argon flows through tube 18 at about 1 to 2 meters per second, which is slower than the drop velocity (2–3.5 m/s). Thus, as the droplets 12 enter the argon stream, their diameter/distance ratio initially decreases as they slow down to the speed of the argon stream. However since they then rapidly evaporate in the heated argon, their diameter to distance ratio then increases. If the droplets are sufficiently far apart, the difference between the argon and droplet velocity vectors can be very substantial. If the droplets are close together, as is normally preferred for maximum sample delivery, then preferably the argon velocity may be in the range between 0.5 and 2 times the droplet velocity. Ideally the droplet and gas velocity vectors are relatively closely matched, for maximum sample delivery.

It is desirable that turbulence in tube 18 be minimized. For this reason, passage 22 from which the argon flowing through tube 18 is introduced, is designed as an annulus about tube 18. It will be seen that the internal wall 96 at location 24 where passage 22 joins tube 18 is smoothly contoured, to help avoid turbulence effects which could disturb the droplets. In addition, the outer wall 98 where passage 22 joins tube 18 is also smoothly shaped, again to help ensure laminar flow of the argon through passage 22 and into tube 18. The continually narrowing cross-section of passage 22 from the settling screens 28 to the location 24 ensures gradual acceleration of the argon stream as it moves through passage 22 into tube 18, helping to prevent the flow from separating from the walls of passage 22 and at location 24, thus avoiding local turbulence.

In addition, to help ensure that the droplets 12 are shot down the axis of tube 18, the nozzle 90 is well polished and ends at a sharp right angle.

As indicated, the droplets 12 proceed down tube 18 until they have been totally dried or desolvated, at the dryness or desolvation point D. At point D, the temperature of the micro particles rapidly increases from a value below the boiling point of water to 700° C. (the temperature of the argon carrier gas). The water which was formerly in the micro particles 12 is now entrained as water vapour dispersed in the argon gas in tube 18.

In the past, e.g. when nebulizers were used to produce liquid samples, others had thought that it was necessary or highly desirable, in order to reduce oxide interference effects, to remove the water vapour in the carrier gas, e.g. by extracting the water vapour through a semi-permeable membrane, or by condensing it on a cold wall. The applicants have found that removal of the water vapour is not necessary. However, it is noted that when the dried micro particles **12*a* reach the plasma 44, they vaporize at a vaporization point Q. An advantage of the method and apparatus described is that the position of the desolvation point D (which is actually a very small region) is controllable by selection of the argon flow rate, temperature in tube 18, and length of tube 18 so that point D can (thanks to the uniform drop size) occur at a selected distance upstream of the entry into the hot plasma. So long as liquid water is present, the micro drop or droplet remains below the boiling point. Thus, even volatile sample components such as mercury or zinc remain in the micro droplet and are not evaporated until the particle becomes dry. Therefore, the unwanted water spreads radially away before all components of the sample begin to evaporate, reducing the central water vapour concentration while keeping the vaporized sample more concentrated centrally, an optimum situation for analytical purposes. The desolvation point D should preferably be spaced sufficiently upstream from the vaporization point Q, e.g. by about one or two centimetres (depending on the velocity of the carrier gas and particles), to allow time for the water vapour from the micro particles to diffuse away from the micro particles, so that the water vapour is not concentrated in the micro region surrounding each micro particle when the micro particle begins to vaporize. This considerably reduces oxide interferences (i.e. production of oxides in the plasma), as contrasted with vaporizing micro particles which contain water. This optimization cannot be obtained to the same degree with poly dispersed or radially spatially distributed droplets or micro particles. For this purpose, tube 18** may typically be about 20 cm long, although this can vary depending on the gas speed and the argon temperature.

It will be appreciated that in the method and apparatus described, since the uniform size and trajectories of all sample droplets create substantially invariant D and Q points or regions for every sample droplet, therefore the D and Q points can be independently controlled, since the D point depends on the size and speed of the droplet, the temperature of the argon gas in which it is entrained, and the length of tube 18, and the Q point depends on the positioning of the plasma and the diameter of the injector tube 38. For example, when the injector tube diameter is 2 mm, as compared with a 5 mm diameter for tube 18, the ratio of the areas of these tubes is 6.25/1, so the argon velocity through tube 38 will be about 6 times as fast as that of the argon in tube 18, subject to any decrease in velocity caused by cooling of the argon by the time it reaches injector 38. The increased velocity can be used (depending on the injector tube diameter) to push the Q point farther downstream (closer to orifice 60).

Some of the advantages of the system described, as contrasted with the use of a nebulizer, will now be explained. Reference is next made to FIG. 4, which plots signal on the vertical axis and time on the horizontal axis. FIG. 4 illustrates one of the problems with nebulizers (which produce a dispersion of droplet sizes) by illustrating at 99 the passage of a droplet which is larger than normal. The passage of such droplet is observed using a laser, and peak 100 (which is an optical laser signal) occurs when the droplet passes through the field of view. Curve 102 is an ion emission signal, and dips substantially as indicated at 104 when the larger droplet passes through the observation point. At the same time, curve 106 which is the atomic emission signal, increases at 108, indicating that the cooling effect of the larger droplet produces an increase in atomic emission as well as a decrease in ion emission. The observed signal when a nebulizer is used consists of an overlay resulting from the drying of a multitude of drops at varying positions due to their varying sizes, leading on average to an undesirable enhancement of oxide formation.

FIG. 5 is a comparison of the concentration response for a prototype of the system described, as compared with a nebulizer, using rhodium (Rh) as a test sample. The concentration response curve for a nebulizer is plotted at 110 in FIG. 5, and that for the prototype for the system described is plotted at 112. It will be seen that the responses to changes in concentration are approximately the same for both systems, as the inventors expected.

Table I below lists experimental results for a prototype system of the kind shown in FIG. 1, for three different drop frequencies and two diameters of injector tube 38. For comparison, the corresponding results when a nebulizer liquid sample source was used, are also listed. Note that a higher drop frequency (drops per second) with the drop size constant corresponds to a higher sample flow.

TABLE I

| | Prototype (1) | Prototype (2) | Prototype (3) | Nebulizer (4) |
|---|---|---|---|---|
| drop size and frequency | 54μ at 1300 dps | 54μ at 1000 dps | 48μ at 500 dps | — |
| tube 18 temperature profile (°C.) | 650–690 | 650–690 | 650–690 | — |
| "nominal" temperature of tube 18 or nebulizer | 700 | 700 | 700 | 25 |

TABLE I-continued

|  | Prototype (1) | Prototype (2) | Prototype (3) | Nebulizer (4) |
|---|---|---|---|---|
| (°C.) |  |  |  |  |
| injector tube 38 dia (mm) | 2.5 | 2 | 2 | 2 |
| (mm) |  |  |  |  |
| sample flow (ml/minute) | .0064 | .0049 | .0017 | .457 |
| sample concentration (parts per billion or ppb) | 400 ppb Rh | 400 ppb Rh | 400 ppb Rh | 400 ppb Rh |
| ion counts per second | $1.23 \times 10^5$ | $8 \times 10^4$ | $3.6 \times 10^4$ | $6 \times 10^4$ |
| ion counts per mg of samples used | $2.3 \times 10^{11}$ | $1.97 \times 10^{11}$ | $2.6 \times 10^{11}$ | $1.6 \times 10^9$ |
| ion counts/sec/ppm Rh | $3 \times 10^5$ | $2 \times 10^5$ | $9 \times 10^4$ | $1.5 \times 10^5$ |
| noise rms/mean | 1.00% | 1.00% | 0.70% | 2.60% |
| Response time: |  |  |  |  |
| Rise | 1 sec. | 1 sec. | 1 sec. | 2 to 3 sec. |
| Fall | 1 to 2 sec. | 1 to 2 sec. | 1 to 2 sec. | 8 sec. |

It will be seen e.g. from columns 2 and 4 of Table I that with a sample flow only 1% of that used in the nebulizer, the prototype produced an ion count about one third higher. (Rhodium was used as a typical analyte.) This was likely due to the combined effect of complete elimination of the sample wastage, and perhaps a better optimization of the analyte concentration.

Figure 6:
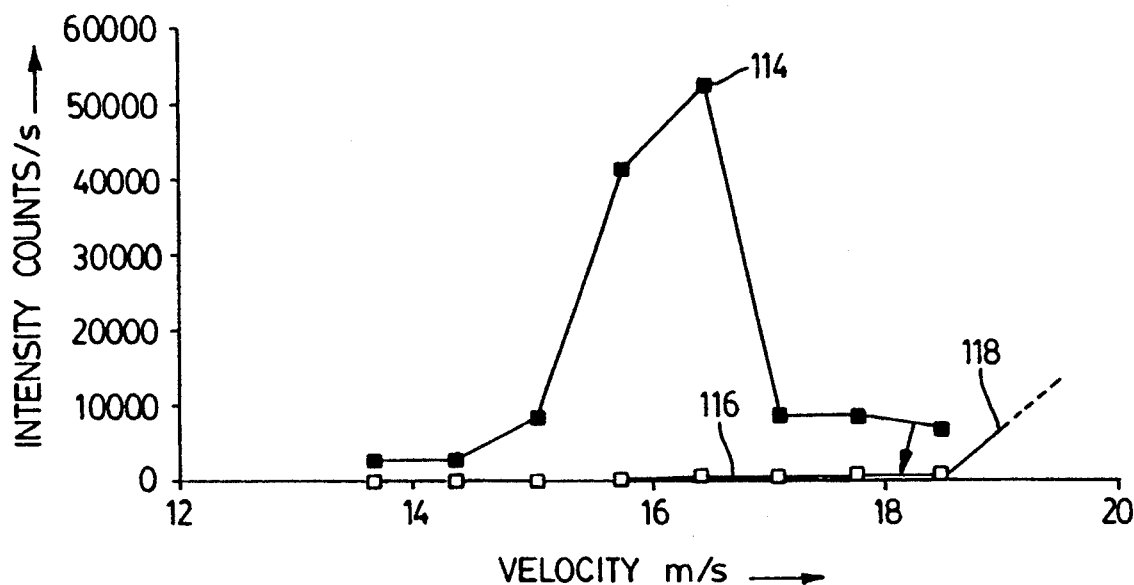

FIG. 6 is a plot of Rh intensity versus velocity, for the argon gas temperature (in the tube 18) of 750° C., with 1250 dps, a 2.5 mm injector, and a 400 ppb solution of Rh. Tube 18 was 25 cm long. The velocity is that calculated to occur in the injector tube 38. It will be seen that as velocity increases, the ion signal (counts per second) also increases. However it is seen that the ion signal peaks at point 114 and then drops rapidly. It is believed that the peak is simply caused by the known effect in which, when the particle is introduced into the torch at higher speed, the plume of vapour produced by the particle has less time to broaden in a downstream direction and therefore a higher proportion of the ions produced travel through the orifice 60. However, if the particle speed is too high, then there is insufficient time for ionization before the ions reach the orifice 60, and therefore the signal drops.

It is noted that in conventional plasma mass spectroscopy, oxide formation is a recurring problem. Oxides form which may have masses similar to those of substances to be observed, and the oxide peaks can obscure the presence or absence of peaks of substances whose presence the investigator wishes to determine. A commonly occurring oxide is cerium (Ce), a natural trace element which is found in many samples. Therefore, for test purposes, the sample solution used in the test prototype of FIG. 1 included, in addition to 400 ppb Rh, 400 ppb Ce.

In FIG. 6, the CeO intensity is shown at 116. It will be seen that the CeO intensity remains low for a range of velocities extending beyond peak 114, and begins to increase (as shown at 118) only well beyond the peak 114.

Figure 7:
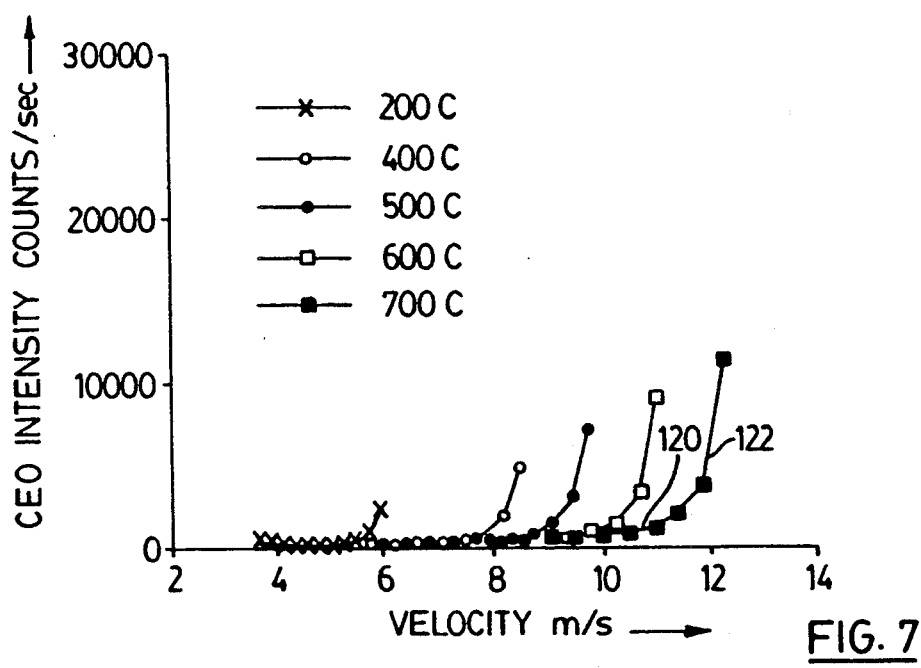

Reference is next made to FIG. 7, which shows a plot of CeO intensity versus carrier gas velocity in tube 18 at the various temperatures noted in the drawing, ranging from 200° C. to 700° C. for the carrier gas in tube 18. It will be seen that for each curve in the drawing there is a low flat part, indicated e.g. at 120, where the CeO signal is very small, and that the curves then bend sharply upwardly, e.g. as shown at 122. The low flat part of each curve corresponds to dry micro particles 12a entering the plasma 44. The steeply rising portion 122 corresponds to liquid water entering the plasma, i.e. in this region the micro droplets 12 have not been fully dried before they enter the plasma. In this case (i.e. wet particles entering the plasma), the product of the concentrations of Ce and 0 would be larger than when the oxygen is diffused throughout the argon stream, and it is this product concentration that generates the CeO production.

It will be seen that as the carrier gas temperature increases, the velocity can increase before there is a significant rise in CeO. This is because at higher carrier gas temperatures, the droplets 12 drymore quickly and can therefore travel at higher speed and yet still enter the plasma after the dryness point D has been reached. However if the D point is too close to the Q point, the water vapour will not have had sufficient time to diffuse away from the micro particles 12a, and higher oxide production may occur.

Figure 8:
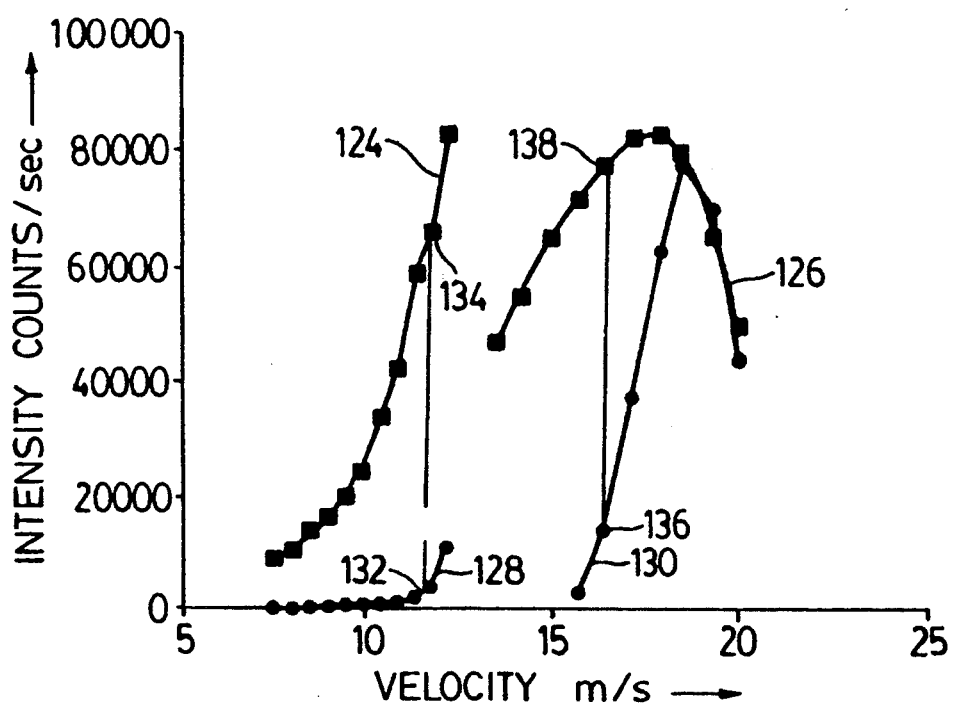

Reference is next made to FIG. 8. FIG. 8 shows two curves 124, 126 of Rh versus velocity. Curve 124 was created using a 2.5 mm injector tube 38, while curve 126 was created using a 2.0 mm injector tube and hence was at higher velocities. FIG. 8 also shows two curve 128, 130 of CeO, again with the 2.5 mm and 2 mm injectors 38 respectively.

It will be seen that for curves 124, 128, the knee 132 of the CeO curve 128 occurs at a point 134 which is relatively high on the Rh curve 124. The same result occurs for curves 126, 130, i.e. a relatively low point 136 on the CeO curve occurs at a relatively high point 138 on the Rh curve 126. All of the curves in FIG. 8 were generated using 400 ppb, Rh and Ce in the sample, 1,000 dps, and an argon gas temperature of 700° C.

The FIG. 8 curves indicate that it is possible to optimize the system to produce a relatively high level of signal while keeping the oxide level relatively low, e.g. by controlling the carrier gas velocity. Thus oxide interferences can be reduced.

Although FIG. 8 illustrates the suppression of CeO counts at high Rh counts, it does not represent the best that can be achieved. The tube 18 used in FIG. 8 was only about 10 cm long. The D and Q points can be further separated at a given argon speed and temperature by simply lengthening the tube 18 and hence increasing the drying time. The effect of increasing the length of tube 18 to about 25 cm is shown in FIG. 6, where it is seen that the CeO curve 116 remains very small throughout the whole useable speed range. This is in sharp contrast to the results obtained with a nebulizer, where the CeO count is much higher.

Further, it is well known that addition of nitrogen to the argon plasma can help mitigate the oxygen interference problems when using a conventional nebulizer. This same technique can be used in the present invention. Tests were conducted, again using an equimolar mixture of 10 ppb Rhodium and 10 ppb Cerium, on a commercial ICP/MS (inductively coupled plasma/mass spectrometer) instrument produced by Sciex division of MDS Health Group Limited of Thornhill, Ontario, Canada under its trade mark Elan 5000. The resultant ratios of $CeO^+/Rh^+$ were as follows:

(a) using conventional nebulizer: $CeO^+/Rh^+ = 4\%$
(b) using dried particle stream as described, with argon only: $CeO^+/Rh^+ = 0.4\%$
(c) using dried particle stream as described, with argon and nitrogen: $CeO^+/Rh^+ = 0.13\%$ It will be seen that the use of a dried particle stream as described reduced observed oxides by a factor of 10. Adding nitrogen to the argon stream reduced the oxides by a further factor of about three.

It is important to note that after all water has been removed from particles 12, it is important to prevent cooling of the carrier gas which would permit recondensation of the water on or in the particles. Thus, for example, the injector tube 38 should be kept sufficiently hot to avoid such undesirable cooling. If such cooling were to occur, detected oxide levels would increase. In addition, the entire apparatus should be insulated (not shown).

Figure 8A:
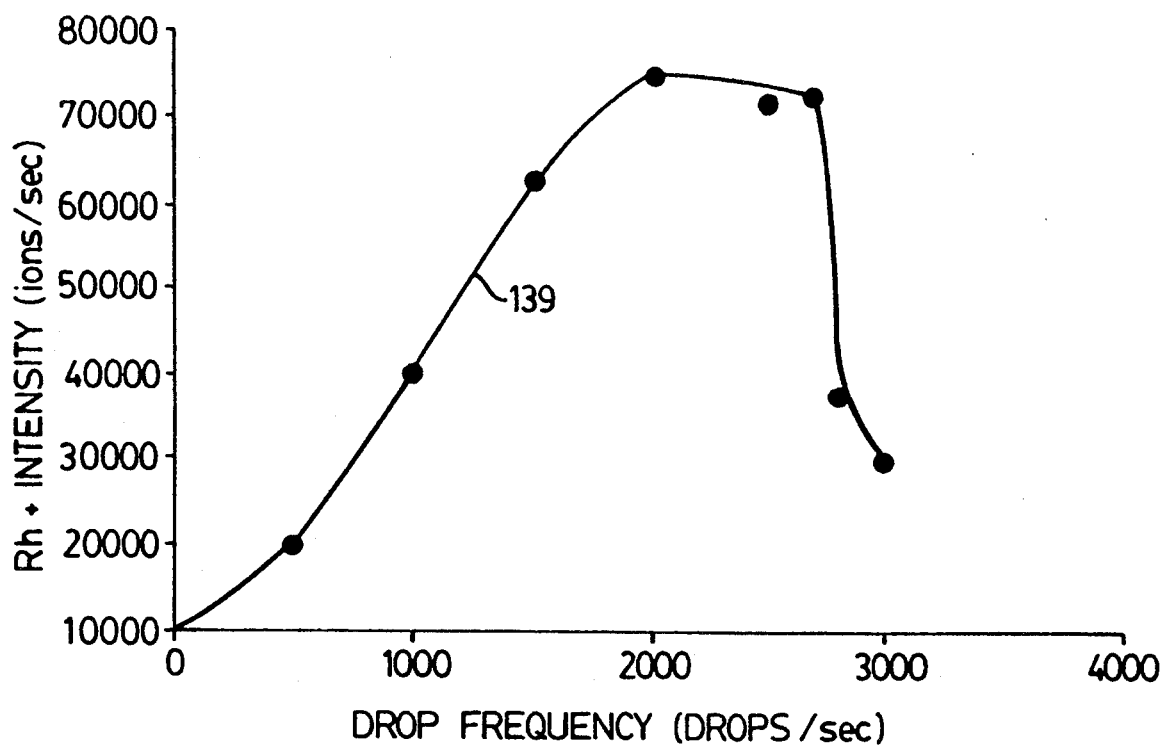

Reference is next made to FIG. 8A, which shows the effect of drop frequency on sensitivity. FIG. 8A was produced using a 1.5 mm diameter injector 38, 60 micron drops, and $Rh = Ce = 10$ ppb. Curve 139 which plots the signal (in $10^4$ counts per second) increases generally linearly with drop frequency, reaching (at about 2000 drops per second) a level of $7.5 \times 10^4$ counts per second. By comparison, a conventional nebulizer typically produces about $2.5 \times 10^4$ counts per second, while using far more sample. Tests with a 2.4 mm diameter injector 38 produced an even higher signal (about 5/3 times the results in FIG. 8A, or about 5 times the nebulizer sensitivity). Increasing the drop size will also produce a larger signal.

It will be seen that using the invention, independent control is available over (a) the sample argon gas flow and velocity, and (b) over the sample loading (controlled by controlling the drop frequency and drop size). Such independent control, which allows the kind of optimization shown for peak 114 in FIG. 6, is not available when a nebulizer is used.

A further feature of the system described is that it can reduce certain acid interferences. Many samples are dissolved in acid, usually sulphuric, hydrochloric or nitric acid. When for example sulphuric acid is used, the SO radical (at 48 amu) can interfere with the observation of desired substances. It is found that the FIG. 1 apparatus reduces the amount of SO observed by a substantial amount (in some cases to zero, in other cases to one quarter or less of the SO observed using a nebulizer). It is believe that this occurred because the heating and drying of the droplets drove away the acid radical before the micro particles 12a reached the plasma.

No similar improvement was observed for the C10 radical, and none was expected for the NO radical, because these radicals are so volatile that they likely quickly dispersed away from the droplets even when a nebulizer was used.

Figure 9:
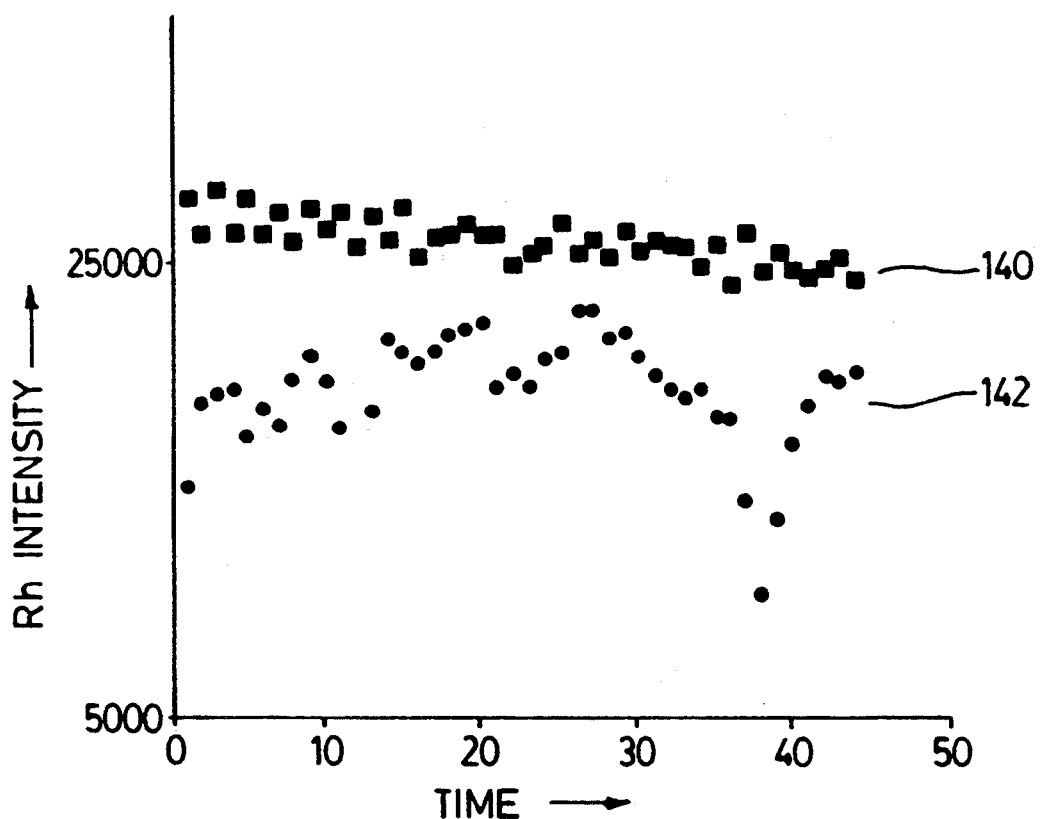

FIG. 9 is a plot showing rhodium signal intensity versus time. Curve 140 is plotted for the FIG. 1 apparatus while curve 142 is a plot produced when a 75 cm flexible tube was inserted between the tube 18 and the torch 36. The flexible tube had a small step connection at each end, creating a sudden enlargement in cross section at the entrance to the flexible tube and a sudden reduction in cross section at its exit. This introduced considerable turbulence into the gas stream, resulting in the very noisy signal depicted by curve 142.

Figure 10:
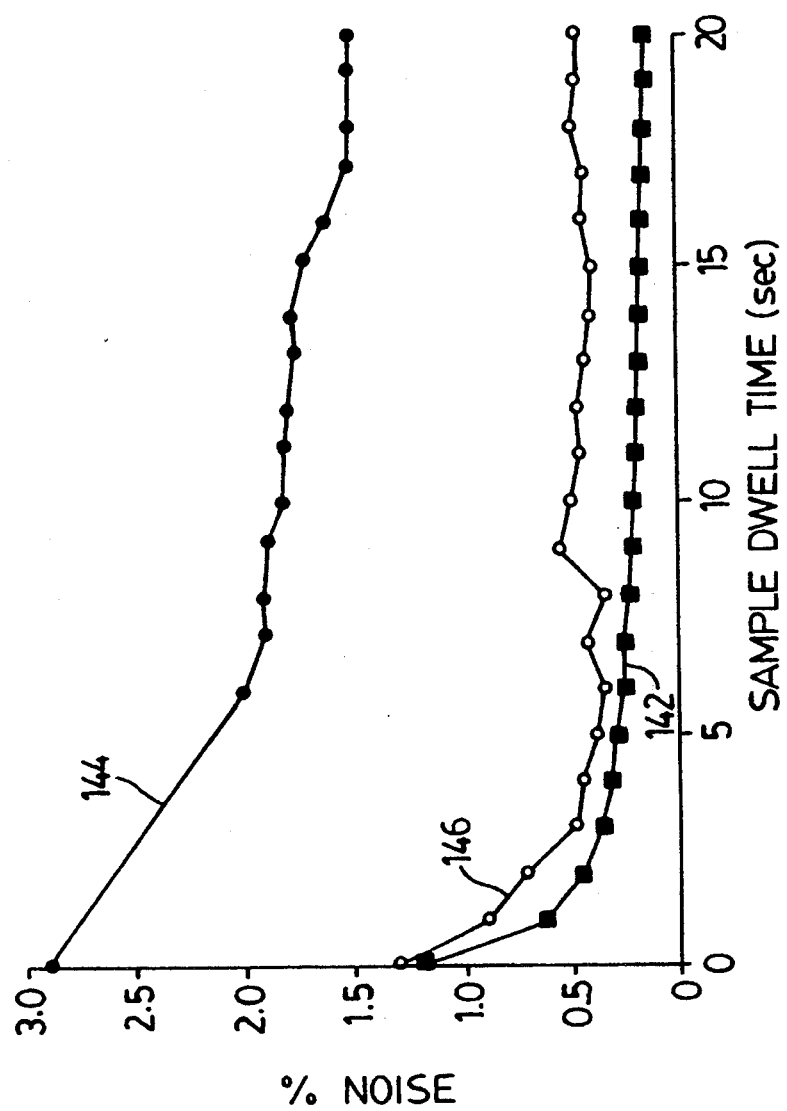
Figure 15:
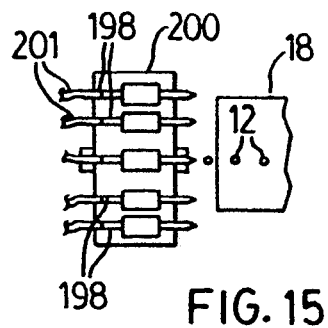
Figure 16:
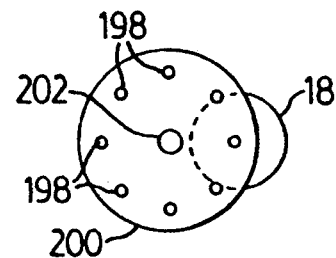
Figure 17:
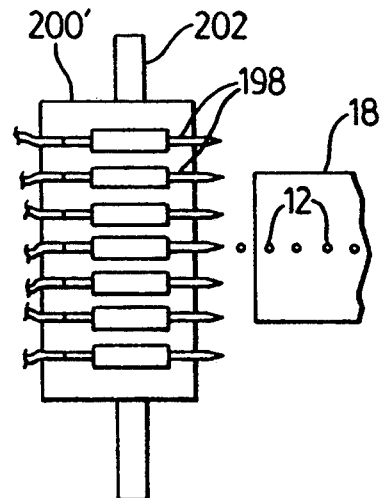
Figure 18:
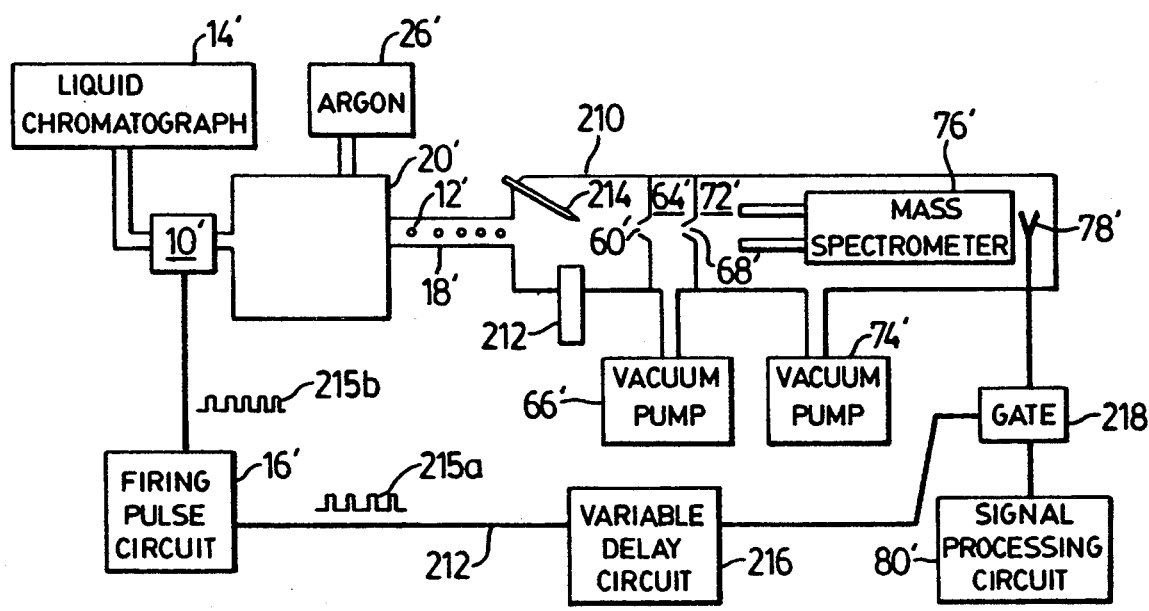
Figure 19:
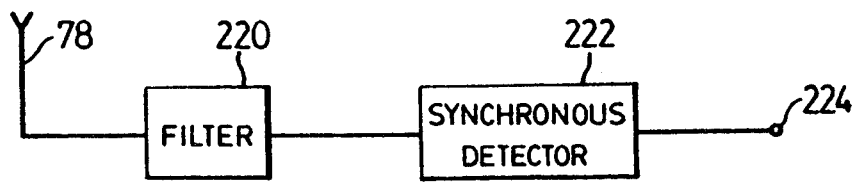

In general, the higher the number of counts which are averaged by the apparatus, the smaller will be the standard deviation in the signal. FIG. 10 shows the relative standard deviation or RSD in percent, normalized, on the vertical axis plotted against counting time on the horizontal axis. The well known counting statistic is indicated at 142. Curve 144 occurs when a nebulizer is used, i.e. the relative standard deviation is never less then about 1.5%. This is caused by the distribution of drop sizes in the spray formed by the nebulizer. Curve 146 was produced using the FIG. 1 apparatus, and as shown in FIG. 10, the RSD can be as low as about 0.5%, or even less. It may in fact be possible to reduce the relative standard deviation for the current apparatus even further, by eliminating any other noise sources which are present.

Reference is next made to FIGS. 11A and 11B, which deal with response time (also shown in Table I). In FIGS. 11A and 11B, ion count rate is plotted along the vertical axis and time along the horizontal axis.

In FIG. 11A, curve 150 shows the ion signal received when a nebulizer is used. When the nebulizer sample flow is turned on, approximately 8 seconds are required for the ion signal to rise to a constant level; the gradual rise in signal is indicated at 152. Then, when the flow is turned off, approximately 2 to 3 seconds (indicated at 154) are required before the signal falls to zero.

In FIG. 11B, curve 156 corresponds to curve 150 but shows the ion signal received when the FIG. 1 apparatus is used. As shown at 158, the signal, when the sample flow is turned on, rises to its peak level in approximately 1 second. Similarly, when the sample flow is turned off, only about 1 second or less (shown at 160) is required for the signal to reach a zero level. Because the flow more closely approximates a step function, much less time is required between samples.

The shorter time needed between samples can significantly increase productivity. For example, samples are commonly introduced (FIG. 12) in a tube 162 as separate liquid "slugs" 164, separated by "slugs" 168 of distilled water. Because the turn on/turn off times are reduced, the length of the water slugs 168 can be reduced, resulting in a higher production rate for the equipment used.

In addition, or alternatively, a multi-nozzle micro pump 170 (FIGS. 13, 14) may be used, containing a number of nozzles 172, 174, 176, 178, 180. Each nozzle 172 to 180 may be connected to a separate chamber 182, 184, 186, etc. and piezo ceramic 192, 194, 196, etc., exactly as used for a multiple nozzle ink Jet printer. Since tube 18 is typically about 5 mm diameter (and can be larger if necessary), and since the nozzles of ink Jet printers are commonly spaced about 1 mm apart, it is easy to place an array of (for example) five nozzles 172 to 180 within the passage 202 leading from the micro pump 170 to the tube 18. It is of course necessary to ensure that the droplets fired from each nozzle do not hit the wall of the tube 18. However, as shown in FIG. 14, the centre nozzle 172 can be aligned with the axis of tube 18, and the four outer nozzles 174 to 180 can be aimed at a very slight angle to that axis, since the droplets fired from them will be entrained in the argon gas flowing around corner 24, and will not (provided that the angle is sufficiently shallow) hit the wall of tube 18. Using the FIGS. 13 and 14 arrangement, different samples can be introduced in rapid succession, simply by turning one nozzle off and turning another on. Alternatively, samples of different substances can be interspersed by firing the liquid jets in an alternating fashion, in situations where this is desired (e.g. to compare different samples or for calibration purposes).

When different kinds of solutions, or different nozzles, are used to form drops, the dryness point D may vary depending on the drop size and the amount of water in the drop. The tube 18 will normally be made long enough so that all drops of interest will be fully dried sufficiently before they reach the vaporization point Q, so that oxygen radicals will have time to diffuse away from the dried particles before they reach point Q.

As an alternative to the FIGS. 13 and 14 arrangement, a circular array of micro pumps 198 may be provided as shown in FIGS. 15 and 16. Micro pumps 198 are arranged around the periphery of a housing 200 rotatable about an axis 202, so that any desired micro pump 198 can be indexed into position to fire droplets into tube 18. It is noted that accuracy of aiming is extremely important, since misalignment can affect sensitivity and hence the quantitative calibration of the instrument. If the consistency of aim of the micro pump is made sufficiently high that calibration of one suffices for the other, then only one micro pump can be used for calibration. Otherwise, each can be calibrated, and then indexing from one micro pump to another (each containing a different sample solution) can be simple and fast. This capability may be used to advantage in automated sample handling systems. Flexible hoses 201 connect micro pumps 198 with fluid reservoirs (not shown). Rotation of housing 200 is limited to 180° in each direction, which can be accommodated by hoses 201.

FIG. 17 shows an array of micro pumps 198' mounted on a housing 200' movable vertically on track 202. Each micro pump can thus rapidly be indexed into position to shoot droplets 12 into tube 18, with less disturbance to hoses 201' than in the FIGS. 15, 16 case.

While the apparatus shown in FIG. 1 employs a plasma to vaporize and ionize the dried micro particles 12, other appropriate means may be used. For example, as shown in FIG. 18, in which primed reference numerals indicate parts corresponding to those of FIG. 1, the dried micro particles **12*a*' may be fired into a chamber 210 and vaporized by a laser 212. Additional ionization can be produced using a corona discharge from a needle 214** connected to a suitable voltage, or using other appropriate means.

In addition, if desired, the signal produced at ion detector 78' can be gated to be synchronized with the passage of the micro particles **12*a*', so that the apparatus measures the signal when ions from the particles 12*a*' reach the mass spectrometer, but not during times between the arrival of such particles. Provided that the particles arrive at regular intervals, this helps to ensure that the desired signal, and not undesired quantities, are measured. As shown in FIG. 1, synchronization apparatus for this purpose can include a lead 212 connected to the pulse generator 214 which powers the micro pump 10'. The lead 212, which carries signals 215*a* timed to coincide with the pulse signals 215*b* which fire the droplets 12', passes through a variable delay circuit 216 and then to a gate 218 which is connected in the line between the detector 78' and the signal processing circuit 80'. The delay circuit 216 is adjusted to maximize the signal produced by detector 78' from the droplets 12' (using a calibration sample), taking into account the delay between the time when a pulse is generated and the time when ions from the resultant droplet, transformed into a dried and then vaporized micro particle, reach the detector 78'. The interval during which gate 218 is open may also be adjusted to optimize the system. The same synchronizing feature may be used with the FIG. 1** apparatus.

While the synchronization method just described will improve the signal to noise (s/n) ratio appreciably, e.g. by a factor of 2, the s/n ratio can be further improved by noting that the method and apparatus described produce an inherently periodic or modulated signal, i.e. the signal is modulated at the drop frequency (typically about 1 KHz). As is well known, the s/n ratio in a modulated signal can be greatly increased by synchronous detection of the modulated signal via a narrow bandpass filter. Thus, as shown in FIG. 19, the signal from detector 78 is passed through a narrow band filter 220 (e.g. a 50 Hz bandwidth about a 1 KHz center frequency, assuming that the drop frequency is 1 KHz). The filtered signal is then synchronously detected by a synchronous detector 222. The resulting output signal at 224 will be expressed in counts per second at that frequency, composed of the desired signal plus any noise which happens to be in the filter band-pass, but with noise contribution at all other frequencies removed. Appropriate calibration will yield the sample concentration of interest. If the noise in the system were white noise, this process can typically improve the s/n ratio by a factor of about 100. It could for example substantially reduce the effect of photon noise, which has been a serious problem in the past.

It is noted that if a nebulizer were used, then in order to use the narrow band-pass filtering technique described, it would be necessary to gate the ions as they are directed into the mass spectrometer, creating artificial modulation. This would create a signal loss and may create other adverse effects as the grid which blocks the ions is turned on and off. With the method and apparatus described, since the modulation is intrinsic, no artificial modulation is needed and no signal is lost. It is noted that the drop frequency should not coincide with known strong noise frequencies such as the flicker frequency of the plasma; if necessary, the drop frequency can be adjusted to avoid this.

It will be appreciated that an advantage of the FIG. 1 embodiment lies in the bunched form of the ion flux produced. With quadrupole mass spectrometry, this embodiment can be combined with a fast acting pulsed micro valve at the sampling orifice, to increase the overall ion-to-gas ratio into vacuum (the signal to vacuum pump requirement ratio). The resultant ion flux can be utilized in time of flight mass spectrometry, which inherently requires modulation.

A further advantage of the method and apparatus described as compared with a nebulizer is that it intrinsically tends to direct less water vapor into the plasma 44. As an example, assume that the droplet train described above contains 1,000 droplets per second. It would then direct six microliters of water per minute, or $2\times10^{20}$ water molecules per minute, into the plasma. Little or no water would be contributed by the argon carrier gas, which is dry.

A nebulizer supplying the same quantity (i.e. mass) of water in the form of droplets would normally also saturate the argon carrier gas from the nebulizer with water. Assuming room temperature and that the argon carrier gas from the nebulizer is at 100% humidity, then at a typical flow rate of one liter per minute of argon gas flow from the nebulizer, the argon gas would add $5 \times 10^{\circ}$ water molecules per minute to the plasma. Thus, the total from the argon gas and the droplets from the nebulizer would be $7 \times 10^{20}$ water molecules per minute added to the plasma. This is 3.5 times more water than is added by the invention as described, and would usually lead to a higher level of observed oxide interferences.

The previous paragraph assumes that the nebulizer supplies the same mass of water in the form of droplets as the uniform droplet train described above. However it is believed, using commonly accepted figures, that the nebulizer actually must supply about three times as much water in the form of droplets as the uniform droplet train previously described, in order to achieve the same level of signal as the droplet train achieves. It is believed that the reason for this is that the droplets from the nebulizer, and hence the resultant particles, have a distribution of sizes and are also more spread out radially than the droplet train (where the droplets and resultant particles are on a common axis). Thus, when the particles from the nebulizer enter the plasma, the smaller particles will flash to vapor sooner than the larger particles, spreading out the distribution of resultant ions axially in the plasma. The ion distribution is also spread out radially, due to the radial distribution of particles from the nebulizer. Since the ion flux in the plasma resulting from the uniform droplet train is more concentrated, a higher ion signal results from a smaller quantity (mass) of droplets.

Assuming that the nebulizer requires three times as much water as the droplet train to produce the same ion signal, and assuming as before that the droplet train supplies $2 \times 10^{20}$ water molecules per minute, this means that the nebulizer droplets supply $6 \times 10^{20}$ water molecules per minute. Since the argon carrier from the nebulizer supplies $5 \times 10^{20}$ water molecules per minute (as before), thus the total from the argon gas and droplets from the nebulizer is $11 \times 10^{20}$ water molecules per minute, or 5 to 6 times the water burden from the uniform droplet stream. This largely accounts for the observed reduction in oxides of 4 to 5 times, because since the particles are kept dry, the oxide levels result primarily from the level of oxygen fed into the plasma.

Figure 20:
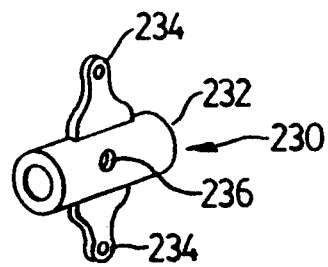

Reference is next made to FIG. 20 which shows a typical graphite furnace 230 used in the well known process of graphite furnace atomic absorption. The graphite furnace 230 consists, as is well known, of a graphite tube 232 connected to electrodes 234 and with a small hole 236 in the wall of tube 232. In normal graphite furnace atomic absorption, a stainless steel pipette is inserted through hole 236 to deposit a sample droplet on the interior wall of tube 232. Electric power is then applied to heat the graphite to drive the water off, and then the power is rapidly increased to flash the graphite to white heat (e.g. 3000° C.). This reduces the sample to atoms. A selected light source (not shown) is then shone axially through the tube, and resonant absorption of lines in the light passing through the tube is detected by a spectroscope (not shown). Alternatively, the spectroscope may utilize the emission spectra created when the sample is vaporized.

A problem with conventional graphite furnace atomic absorption spectroscopy is that although graphite is relatively inert, it is not completely inert and can interfere with the spectrum produced. In addition, since the graphite furnace must be flashed very rapidly to white heat, the graphite furnace must be very small.

Figure 21:
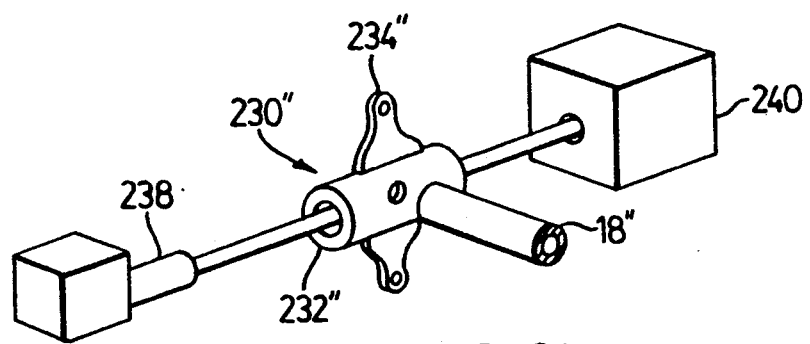
Figure 22:
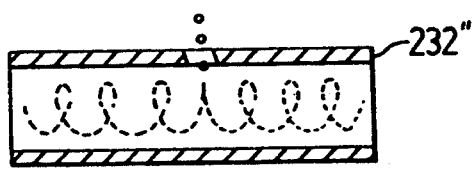

According to the invention, and as shown in FIGS. 21 and 22, where double primed reference numerals indicate parts corresponding to those of the previous drawings, tube 18″ can be arranged to fire micro particles through hole 236″ into the interior of tube 232″ (together with a flow of argon). The tube 232″ can be maintained at a high temperature, e.g. 3000° C. (and can be largely enclosed and surrounded with an inert gas to prevent oxidation). The argon in tube 232″ will spiral toward both ends of the tube, as shown in FIG. 22, while the micro particle entering the tube will vaporize, producing an emission or absorption spectrum as before. The spectrum can be observed by directing light from an appropriate light source 238 into one end opening of tube 232″ and observing the new resultant absorption spectrum with an optical spectrometer 240 which receives light from the other end of tube 232″. Alternatively, the emission spectrum produced when the sample is vaporized can be detected using the spectrometer 240.

Since the micro particles entering graphite furnace 230″ will not normally contact the walls of the furnace, but instead will spiral around inside the walls, the problem of wall interferences, and also deposition of material on the walls, is reduced.

In addition, productivity is greatly increased since the process has been converted from a slow batch process to a more continuous process.

Figure 23:
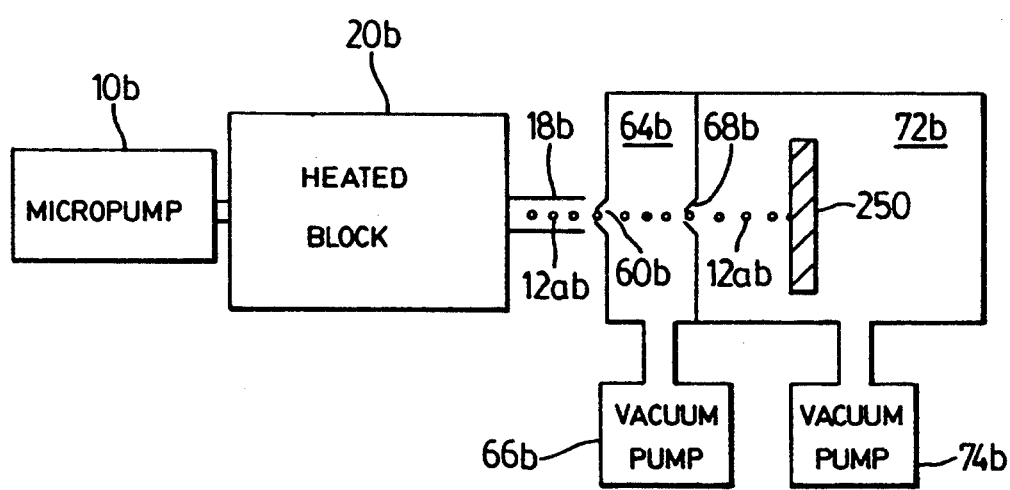

While the embodiments described have used the dried particles for analysis purposes, these particles may also be used to deliver controlled micro-dosages of substances onto a controllable micro-region of a surface in vacuum. For example, ion beams are currently used for ion implantation into semiconductor surfaces, at a low doping rate. Vapour deposition is also used, at a high flux rate, with masks. With the present invention, as shown in FIG. 23, where reference numerals with the suffix "b" correspond to those of FIG. 1, dried particles 12ab are injected directly through orifice 60b, first vacuum chamber 64b, and orifice 68b into second vacuum chamber 72a.

A member 250, on the surface of which material is to be deposited, is located in vacuum chamber 72b. Member 250 is mounted for movement by conventional means, not shown, so that as dried particles are directed at its surface, it can be moved to produce a desired pattern of deposition. As member 250 is moved, the frequency of dried particles 12ab can be controlled so that the amount of material deposited on the surface of member 250 at any given location can be controlled as desired. After deposition, the surface of member 250 can be annealed or otherwise treated as needed. Since the deposition process can use a single micro particle, several micro particles, or a stream of micro particles at any desired frequency over a considerable range, very close control may be achieved over the deposition of material on the surface of member 250.

Figure 24:
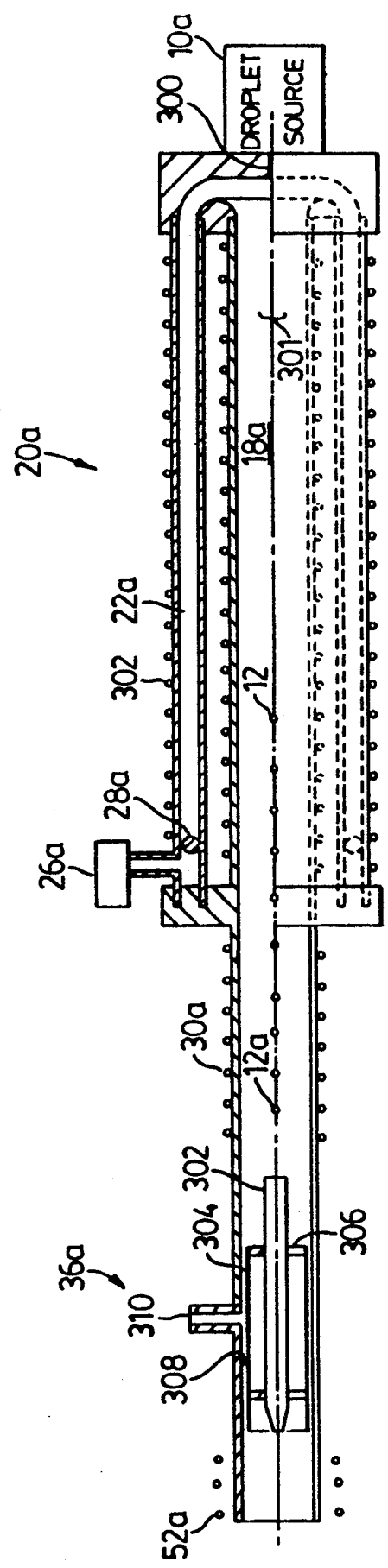

Reference is next made to FIG. 24, which shows a form of apparatus according to the invention suitable for use not only with a stream of droplets aligned on an axis, but also with a spray produced by a nebulizer. In FIG. 24 parts corresponding to those of FIG. 1 are indicated by reference numerals with a suffix "a".

In FIG. 24, the droplet source 10a can be a micro pump as described previously, or it can be any form of conventional nebulizer, e.g. a spray (i.e. pneumatic) nebulizer, or an ultrasonic nebulizer. Droplets from the droplet source 10a are directed through a narrow (e.g. 4 mm diameter) passage 300 into tube 18a.

Tube 18a, instead of being relatively narrow (e.g. about 5 mm inner diameter) as before, is now of much greater inner diameter, e.g. about 18 mm. As before, the stream of carrier gas flowing through tube 18 is laminar, so the stream of droplets, whether dispersed along a single axis or in the form of a spray, is carried along the central portion 301 of the flow in tube 18a and is not dispersed to the periphery of the flow (since there is no turbulence). As before, the droplets are heated or baked thoroughly by heater 30a extending along tube 18a, and also by heat supplied from an external heater 302 which heats the carrier gas flowing into tube 18a. This ensures that all of the water present in the droplets is removed. In the version of the invention described in FIG. 1, the carrier gas flow through tube 18 was typically about one liter per minute. The torch 36 typically utilizes about 15 liters of argon per minute, supplied at the rate of about one liter per minute through injector tube 38, about 0.8 liters per minute through tube 40, and about 13 liters per minute supplied through tube 42. The outer flow through tube 42 is of relatively high velocity and cools the quartz tube of the torch and supplies some of the gas for the plasma 44. The inner or central flow through injector tube 38 contains the sample and penetrates into the plasma (and is therefore of higher velocity than the intermediate flow) to inject the sample into the plasma. The intermediate or auxiliary flow through tube 42 is of low velocity and is believed to assist ignition and to improve the plasma characteristics.

In the FIG. 24 embodiment, all or most of the total flow for the torch is directed through tube 18a. In the example given above, approximately 10 to 15 liters of argon per minute is directed through tube 18a. Therefore, water vapor removed from the micro particles 12a is now dispersed in 10 to 15 times more volume than in the FIG. 1 version. Thus, since there will be less water vapor in the micro vicinity of the particles when the particles are vaporized, the level of oxides produced in the plasma is reduced.

The gas flow through tube 18a has the normal parabolic pipe flow velocity profile, and the velocity at the center of tube 18a is relatively low, e.g. of the order of 3 meters per second. Therefore this gas flow must be reconfigured to have the desired velocity profile for the torch 36a. In FIG. 24 this is accomplished by providing, at the end of tube 18a which enters the torch, an inner tube 302 and an intermediate tube 304. Inner tube 302 has an inner passage which conducts the dried particles 12a with a flow of about one liter per minute into the plasma. Inner tube 302 may have an inner diameter of 4 to 5 mm at its entrance, and is necked down to 2 to 2.5 mm at its exit. Intermediate tube 304 may have an inner diameter of about 14 mm and an external diameter of about 16 mm. Tube 304 has, between its inner periphery and the outer periphery of tube 302, an air flow filter disk 306 (which can be a porous material or can simply consist of a quartz or glass wall with holes formed in it) which reduces the velocity and volume of gas travelling through tube 304. The remainder of the flow travels through the space 308 between the outer periphery of tube 304 and the inner periphery of tube 18a. The space between the peripheries of tubes 18a and 304 may typically be of the order of about 1 mm. The dimensions of the various components are configured to provide the desired flows, e.g. about one liter per minute through tube 302, about 0.8 liters per minute through tube 304, and the remainder of the flow between tubes 304 and 18a. If additional gas is needed to control the characteristics of the torch, and e.g. to provide the swirl which is thought desirable, this gas can be provided through a control gas inlet 310.

Typically the approximate gas velocities thus produced are: at the exit of central tube 302, 15 meters per second; through intermediate tube 304, 0.3 meters per second, and through the space 308, 14 to 15 meters per second (including the control gas).

It will be seen that most of the flow from tube 18a travels through space 308. Only a minor portion (the central portion) travels through tube 302, and disk 306 allows little gas to flow through it into tube 304, deflecting most of the flow through space 308. The control gas inlet 310 is normally offset to impart the usual desired swirling motion to the outer flow, and the control gas need normally not be heated.

As indicated previously, the oven 20a and the portion of tube 18a projecting from it are both insulated to prevent cooling of the carrier gas before it enters the plasma, to avoid recondensation of water onto the dried particles.

An advantage of the FIG. 24 arrangement is that, as mentioned, it can accept mono-dispersed particles, or spray from any form of nebulizer; it reduces oxides detected by dispersing the water vapour in a much larger volume of carrier gas, and it helps to avoid cooling of the injector tube 302 by bathing the outside of the injector tube with heated carrier gas. Preferably the inner diameter of tube 18a is at least twice that of the central portion 301, and desirably it should be at least three times that diameter, for greater dilution of the water vapor. In the example given, central portion 301 is 5 mm in diameter, while tube 18a has as mentioned an 18 mm inner diameter.

While preferred embodiments of the invention have been described, it will be appreciated that various changes may be made within the scope of the appended claims.

We claim:

1. A method of sampling a liquid solution containing dissolved solids, comprising:

(a) producing a stream of laminarly flowing carrier gas travelling in a predetermined direction at a selected speed, (b) producing a linear stream of spaced small droplets from said solution, said droplets being of substantially equal size and being uniformly spaced apart in single file on a common axis and travelling in said predetermined direction at a speed which does not differ substantially from said selected speed, (c) introducing said stream of droplets in said predetermined direction into said stream of carrier gas and transporting said droplets with said carrier gas, the substantial equality of the speed and direction of said droplets with the speed and direction of said laminarly flowing carrier gas minimizing production of wakes by said droplets in said carrier gas, (d) heating said carrier gas and thereby heating said droplets therein, to evaporate water from said droplets into said carrier gas, (e) transporting said droplets in said carrier gas until said droplets have substantially dried to form a stream of uniformly spaced, equal size dried particles arranged in single file on an axis, said particles containing solids from said solution, (f) vaporizing said dried particles to produce vapor therefrom, (g) and analyzing said vapor.

2. A method according to claim 1, wherein the velocity of said stream of carrier gas is slightly less than the velocity of said droplets when said droplets are introduced into said carrier gas.

3. A method according to claim 1 wherein said step of vaporizing said particles is performed at a location spaced downstream along said stream of carrier gas from the location at which said particles are substantially fully dried, to provide time for water vapour from said droplets to diffuse away from said particles before said particles are vaporized.

4. A method according to claim 3 wherein said vapour is ionized, and the resulting ions are analyzed in a mass spectrometer.

5. A method according to claim 3 wherein said vapour is analyzed by light spectroscopy.

6. A method of sampling a liquid solution containing dissolved solids, comprising:

(a) producing a stream of laminarly flowing carrier gas, (b) producing a linear stream of spaced small droplets from said solution, said droplets being spaced apart in single file on a common axis, (c) introducing said stream of droplets into said stream of carrier gas and transporting said droplets with said carrier gas, (d) said droplets being injected into said carrier gas at a velocity of 2 to 4 meters per second, said carrier gas flowing at a velocity of between 1 and 2 meters per second where said droplets are introduced into said carrier gas, the velocity vectors of said stream of carrier gas and of said droplets being substantially aligned, (e) heating said carrier gas and thereby heating said droplets therein to evaporate water from said droplets into said carrier gas, (f) transporting said droplets in said carrier gas until said droplets have substantially dried to form a stream of spaced dried particles, said particles containing solids from said solution.

7. A method of sampling a liquid solution containing dissolved solids, comprising:

(a) producing a stream of laminarly flowing carrier gas, (b) producing a linear stream of spaced small droplets from said solution, said droplets being spaced apart in single file on a common axis, said droplets being between 40 and 80 microns in diameter, (c) introducing said stream of droplets into said stream of carrier gas and transporting said droplets with said carrier gas, (d) heating said carrier gas and thereby heating said droplets therein, to evaporate water from said droplets into said carrier gas, (e) transporting said droplets in said carrier gas until said droplets have substantially dried to form a stream of spaced dried particles, said particles containing solids from said solution.

8. A method of sampling a liquid solution containing dissolved solids, comprising:

(a) producing a stream of laminarly flowing carrier gas, (b) producing a linear stream of spaced small droplets from said solution, said droplets being produced at a rate of between 500 and 8000 droplets per second, (c) introducing said stream of droplets into said stream of carrier gas and transporting said droplets with said carrier gas, (d) heating said droplets in said carrier gas to evaporate water from said droplets into said carrier gas, (e) transporting said droplets in said carrier gas until said droplets have substantially dried to form a stream of spaced dried particles, said particles containing solids from said solution.

9. A method according to claim 8 wherein said droplets are produced at a rate of between 500 and 3000 droplets per second.

10. A method according to claim 8 or 9 wherein said droplets are of substantially uniform size when produced and are spaced apart from each other by substantially equal distances in said stream of droplets and are on a common axis in said stream of droplets.

11. A method of sampling a liquid solution containing dissolved solids, comprising:

(a) producing a stream of laminarly flowing carrier gas, (b) producing a stream of spaced small droplets from said solution, said droplets being produced one at a time, upon demand, by a triggering signal, (c) introducing said stream of droplets into said stream of carrier gas and transporting said droplets with said carrier gas, (d) heating said droplets in said carrier gas to evaporate water from said droplets into said carrier gas, (e) transporting said droplets in said carrier gas until said droplets have substantially dried to form a stream of spaced dried particles, said particles containing solids from said solution.

12. A method according to claim 11 wherein said stream of droplets includes droplets from said liquid solution and other droplets from a calibrating solution, and including the step of using the droplets from the calibrating solution for calibration.

13. A method according to claim 11 wherein said droplets are of substantially uniform size when produced and are spaced apart from each other by substantially equal distances in said stream of droplets and are on a common axis in said stream of droplets.

14. A method according to claim 11 or 13 and including the steps of vaporizing said particles to produce vapor therefrom, and analyzing said vapor, said step of vaporizing said particles being performed at a location spaced downstream along said stream of carrier gas from the location at which said particles are substantially fully dried, to provide time for water vapor from said droplets to diffuse away from said particles before said particles are vaporized.

15. A method according to claim 11 and including the steps of vaporizing said particles to produce vapor therefrom, and analyzing said vapor.

16. A method according to claim 13 or 15, 27, 28 and including the steps of (i) producing at a detector an ion detection signal, (ii) processing said ion detection signal to produce an output signal, (iii) and synchronizing said processing of said ion detection signal with the arrival of ions from said vapour of each particle at said detector, to increase the proportion in said output signal of signal from ions of said particles and to reduce the proportion in said output signal of signal from other sources.

17. A method according to claim 11 and including the step of directing said dried particles into a vacuum and depositing said particles onto a surface located in said vacuum.

18. A method according to claim 11 and including the step of directing said dried particles into a vacuum and depositing said particles onto a surface located in said vacuum, and moving said surface as said particles are deposited thereon to produce a desired pattern of deposition of said particles on said surface.

19. A method according to claim 11 and including the step of directing said dried particles into a vacuum and depositing said particles onto a surface located in said vacuum, and moving said surface as said particles are deposited thereon to produce a desired pattern of deposition of said particles on said surface, and thereafter annealing said surface.

20. A method of analyzing solids dissolved in a liquid sample solution, comprising:
(a) directing said solution into a small chamber,
(b) causing a pressure pulse to be applied to solution in said chamber to shoot a droplet of said solution from said chamber,
(c) entraining said droplet in a stream of flowing carrier gas,
(d) heating said droplet in said stream of carrier gas to evaporate water from said droplet into said carrier gas,
(e) transporting said droplet in said carrier gas until said droplet is substantially dried to form a dried particle containing said solids,
(f) vaporizing said dried particle to produce vapor therefrom,
(g) and analyzing said vapor.

21. A method according to claim 20 wherein said stream of carrier gas is substantially laminar.

22. A method according to claim 21 wherein said droplet is heated by heating said carrier gas.

23. A method according to claim 21 wherein said particle is vaporized at a location spaced downstream along said stream of carrier gas from the location at which said particle is substantially fully dried, to provide time for water vapour from said droplet to diffuse away from said particle before said particle is vaporized.

24. A method according to claim 23 wherein a plurality of solutions are directed into a plurality of said chambers and droplets are shot in a selected order from said chambers, all of said droplets being entrained in said stream of carrier gas.

25. A method according to claim 24 wherein at least one of said solutions is a calibrating solution.

26. A method according to claim 23 and including the steps of shooting droplets of said solution from said chamber into said stream of carrier gas, then moving said chamber to a position where droplets emitted therefrom will not enter said carrier gas, moving a second chamber into a position where droplets emitted therefrom will enter said stream of carrier gas, shooting droplets of another solution from said second chamber into said stream of carrier gas and performing said steps (d), (e), (f) and (g) thereon, and cleaning said first mentioned chamber.

27. A method according to claim 26 wherein said first mentioned chamber is cleaned while droplets from said second chamber are being shot into said stream of carrier gas.

28. A method according to claim 21 wherein a series of said pulses are applied to said solution to produce a stream of said droplets.

29. A method according to claim 26 or 27 wherein droplets first from a calibrating solution, and then from a sample solution, are shot from each chamber into said carrier gas stream, and wherein the droplets from said second chamber are of a sample solution different from the sample solution used to shoot droplets from said first mentioned chamber.

30. A method according to claim 20, 21 or 23 wherein said dried particle is vaporized in a furnace, said vapour being analyzed by light spectroscopy.

31. A method according to claim 23 and including the step of producing a series of said pressure pulses to produce a stream of said droplets, said droplets being of substantially uniform size when produced and being substantially uniformly spaced apart in said stream, thereby producing a stream of said dried particles, said dried particles being of substantially uniform size and being substantially uniformly spaced apart in said stream.

32. A method according to claim 31 and including the steps of directing said stream of dried particles with said carrier gas into a furnace, said graphite furnace being heated to vaporize said dried particles, said vapour being analyzed by light spectroscopy.

33. A method according to claim 20, 23, 31 32 or 15 wherein in said step of analyzing said vapour, a detection signal is produced, and including the steps of producing a synchronizing signal having pulses synchronized with the production of said droplets, and shutting off said detection signal at intervals between said pulses.

34. A method according to claim 3, 31, 32 or 15 wherein in said step of analyzing said vapour, a detection signal is produced, and including the step of filtering said signal in a low pass filter having a pass band which includes a frequency corresponding to the frequency at which said droplets are produced, to produce a filtered signal, and synchronously detecting said filtered signal to enhance the signal to noise ratio thereof.

35. A method according to claim 20, 21, 23 or 31 wherein said vapour is analyzed by light spectroscopy.

36. A method according to claim 20, 21, 23 or 31 wherein said vapour is analyzed by mass spectrometry.

37. Apparatus for analyzing solids dissolved in a liquid solution, comprising:
(a) a chamber for said solution, said chamber having an outlet nozzle, and means for applying a pressure pulse to solution in said chamber to shoot a droplet of said solution from said nozzle at a selected speed,
(b) tube means coupled to said nozzle for receiving said droplet,
(c) means for introducing a stream of carrier gas into said tube means for said carrier gas to flow in said tube means at a selected velocity and to carry said droplet along said tube,
(d) means for heating said droplet in said carrier gas,
(e) said tube means being sufficiently long for substantially all of the water in said droplet to evaporate into said carrier gas leaving a substantially dried particle of said solids,
(f) means connected to said tube means for vaporizing said dried particle,
(g) and analyzer means coupled to said tube means for analyzing the vapour from said dried particle.

38. Apparatus according to claim 37 wherein said means for vaporizing said particle is spaced from the location at which said particle is substantially fully dried, to provide time for water vapour from said droplet to diffuse away from said particle before said particle is vaporized.

39. Apparatus according to claim 38 wherein said means for introducing said flow of carrier gas includes conduit means concentric and coaxial with said tube means, said conduit means joining said tube means at smoothly rounded surfaces, for carrier gas to flow in said conduit means in a direction opposite to the direction of flow in said tube means and then to change direction and flow into said tube means at said smoothly rounded surfaces for said flow of carrier gas in said tube means to be laminar.

40. Apparatus according to claim 39 wherein the cross-sectional area of said conduit means decreases toward said smoothly rounded surfaces, to reduce the likelihood of gas flow detachment from the walls of said conduit means.

41. Apparatus according to claim 38 wherein said means for applying a pressure pulse to said solution includes means for generating a series of uniformly spaced and uniformly sized electrical pulses, means responsive to each electrical pulse for applying a said pressure pulse to said solution thus to produce a stream of said droplets in said carrier gas stream, said droplets being of uniform size when produced and being uniformly spaced apart and on a common axis in said carrier gas stream, thereby to produce a stream of said dried particles, said dried particles being of uniform size and being uniformly spaced apart in said carrier gas stream.

42. Apparatus according to claim 41 wherein said analyzer means includes a mass spectrometer having ionizer means for producing ions from said vapour, ion detection means for producing an ion detection signal from said ions, signal processing means for producing an output signal from said ion detection signal, and gate means coupled between said ion detection means and signal processing means for controlling signal passage between said ion detection means and said signal processing means, and synchronizing means coupled between said pulse generating means and said gate means for synchronizing the processing of said ion detection signal with the arrival of ions from said vapour of each particle at said ion detection means, to increase the proportion in said output signal of signal from ions of said particles and to reduce the proportion in said output signal of signal from other sources.

43. Apparatus according to claim 41 wherein said analyzer means includes means for producing a detection signal, means for producing a synchronizing signal having pulses synchronized with the production of said droplets, and means for synchronizing said detection signal with said synchronizing signal and for shutting off said detection signal at intervals between said pulses, to increase the signal to noise ratio of said detection signal.

44. Apparatus according to claim 41 wherein said analyzer means includes means for producing a detection signal, narrow band filter means having coupled to said detection signal means for filtering said detection signal, said narrow band filter means having a pass band having a frequency corresponding to the frequency of production of said droplets, and synchronous detection means for detecting the signal from said narrow band filter means and for producing an output signal having a signal to noise ratio greater than that in said detection signal.

45. Apparatus according to claim 37 wherein said means for heating comprises means for heating said carrier gas.

46. Apparatus according to claim 37 wherein said analyzer means includes a mass spectrometer having ionizer means for producing ions from said vapour, ion detection means for producing an ion detection signal from said ions, and signal processing means for producing an output signal from said ion detection signal.

47. A method of analyzing solids dissolved in a liquid sample solution, comprising:
(a) producing small droplets from said solution,
(b) producing a single laminar stream of flowing carrier gas having a central portion and an outer portion, said central and outer portions flowing in the same direction at substantially the same speed,
(c) directing said droplets into said central portion of said stream and conveying said droplets in said central portion of said stream,
(d) heating said carrier gas and said droplets to evaporate water from said droplets into said carrier gas,
(e) transporting said droplets in said carrier gas until said droplets are substantially dried to form dried particles containing said solids,
(f) allowing water vapor removed from said particles to disperse away from said particles,
(g) the diameter of said outer portion being substantially larger than that of said central portion, to allow said water vapor to disperse out of said central portion into said outer portion thus to reduce the concentration of water vapor in the immediate vicinity of said particles,
(h) and directing said stream of carrier gas into a torch having a plasma formed therein, and causing said central portion to penetrate into said plasma and causing said outer portion to supply at least a portion of the gas used to form said plasma.

48. A method according to claim 47 wherein the diameter of said outer portion is at least twice the diameter of said central portion.

49. A method according to claim 47 wherein the diameter of said outer portion is at least three times the diameter of said central portion.

50. A method according to claim 47 and including the steps of reconfiguring the velocity profile of said stream adjacent said torch to divide said outer portion into a peripheral portion, and an intermediate portion between said outer and central portions, and imparting increased velocities to said peripheral and central portions and a velocity substantially lower than said increased velocities to said intermediate portion.

51. A method according to claim 47 or 50 wherein said droplets are produced as a stream of uniformly spaced apart droplets on a common axis.

52. A method according to claim 47 or 51 wherein said droplets are produced by nebulization of said sample solution.

53. Apparatus for analyzing solids dissolved in a liquid solution, comprising:
(a) tube means,
(b) means for introducing a stream of carrier gas into said tube means for said carrier gas to fill said tube means and to flow laminarly in said tube means, said stream having a central portion and an outer portion both flowing in the same direction at substantially the same speed as a single stream, (c) droplet means for producing droplets from said liquid solution, (d) means coupling said droplet means to said tube means for introducing said droplets into said central portion of said stream for said droplets to be conveyed in said central portion, (e) means for heating said droplets and said carrier gas in said tube means, (f) said tube means being sufficiently long for substantially all of the water in said droplets to evaporate into said carrier gas and to disperse therein, leaving substantially dried particles of said solids, (g) torch means connected to said tube means for receiving said inner and outer portions of said carrier gas stream and said dried particles, and means for producing a plasma in said torch means to vaporize said particles for analysis, (h) said tube means being of inner diameter substantially larger than said central portion, for allowing water vapor removed from said particles to disperse away from said particles into said outer portion of said stream, to reduce the concentration of water vapor in the immediate vicinity of said particles.

54. Apparatus according to claim 53 wherein the inner diameter of said tube is at least twice the diameter of said central portion.

55. Apparatus according to claim 53 wherein the inner diameter of said tube is at least three times the diameter of said central portion.

56. Apparatus according to claim 53 and including flow profiling means connected between said tube means and said torch adjacent said torch for configuring the velocity profile of said stream to have said central portion, a peripheral portion, and an intermediate portion between said central and peripheral portions, and for imparting substantially higher velocities to said central and peripheral portions than to said intermediate portion.

57. Apparatus according to claim 56 and including means for adding a control stream of carrier gas to said peripheral portion.

58. Apparatus according to claim 56 wherein said droplet means comprises a nebulizer.

* * * * *